United States Patent
Cheng et al.

(10) Patent No.: US 11,299,450 B2
(45) Date of Patent: Apr. 12, 2022

(54) SYSTEM AND PROCESS FOR CO-PRODUCING DIMETHYL CARBONATE AND ETHYLENE GLYCOL

(71) Applicant: INSTITUTE OF PROCESS ENGINEERING, CHINESE ACADEMY OF SCIENCES, Beijing (CN)

(72) Inventors: Weiguo Cheng, Beijing (CN); Li Dong, Beijing (CN); Qian Su, Beijing (CN); Songsong Chen, Beijing (CN); Junping Zhang, Beijing (CN); Suojiang Zhang, Beijing (CN)

(73) Assignee: INSTITUTE OF PROCESS ENGINEERING, CHINESE ACADEMY OF SCIENCES, Beijing (CN)

( * ) Notice: Subject to any disclaimer, the term of this patent is extended or adjusted under 35 U.S.C. 154(b) by 207 days.

(21) Appl. No.: 16/625,376

(22) PCT Filed: Sep. 14, 2017

(86) PCT No.: PCT/CN2017/101784
§ 371 (c)(1),
(2) Date: Dec. 20, 2019

(87) PCT Pub. No.: WO2018/233093
PCT Pub. Date: Dec. 27, 2018

(65) Prior Publication Data
US 2021/0331999 A1    Oct. 28, 2021

(30) Foreign Application Priority Data

Jun. 20, 2017 (CN) .......................... 201710470046.3

(51) Int. Cl.
  *B01J 8/00* (2006.01)
  *B01J 8/02* (2006.01)
  (Continued)

(52) U.S. Cl.
  CPC .......... *C07C 68/065* (2013.01); *B01J 8/0242* (2013.01); *B01J 8/0278* (2013.01); *B01J 8/0285* (2013.01);
  (Continued)

(58) Field of Classification Search
  CPC ..... B01J 8/00; B01J 8/02; B01J 8/0242; B01J 8/0278; B01J 8/0285; B01J 2208/00;
  (Continued)

(56) References Cited

U.S. PATENT DOCUMENTS 6,407,279 B1   6/2002  Buchanan et al.
9,518,003 B1  12/2016  Panchal et al.
(Continued)

FOREIGN PATENT DOCUMENTS

CN    1212252 A    3/1999
CN    1733696 A    2/2006
(Continued)

OTHER PUBLICATIONS

Machine translation of CN 104761429 A, which was provided in the IDS filed on Dec. 20, 2019 and was published on Jul. 8, 2015. (Year: 2021).*

(Continued)

*Primary Examiner* — Natasha E Young
(74) *Attorney, Agent, or Firm* — Bond Schoeneck & King, PLLC; George McGuire

(57) ABSTRACT

A system and a process for co-producing dimethyl carbonate and ethylene glycol. The system comprises an interconnected ethylene carbonate preparation unit and an ethylene carbonate alcoholysis unit. The ethylene carbonate prepara- (Continued)

tion unit comprises a fixed bed reactor and a light-component stripping column connected to each other. The fixed bed reactor is filled with a supported ionic liquid catalyst. The process comprises the steps of: reacting carbon dioxide and ethylene oxide as raw materials in the fixed bed reactor to produce ethylene carbonate, purifying the ethylene carbonate and then mixing it with an alcoholysis reaction catalyst, and reacting the mixture with methanol in a reactive distillation tower, producing dimethyl carbonate and ethylene glycol. The process increases the conversion rate of ethylene oxide and avoids the need for a process of separating conventional homogeneous catalysts from ethylene carbonate, thereby reducing process energy consumption and simplifying process procedures.

23 Claims, 1 Drawing Sheet

(51) Int. Cl.
    *C07C 29/00*   (2006.01)
    *C07C 29/128*  (2006.01)
    *C07C 68/00*   (2020.01)
    *C07C 68/06*   (2020.01)
    *C07C 68/065*  (2020.01)
(52) U.S. Cl.
    CPC . *C07C 29/1285* (2013.01); *B01J 2208/00026* (2013.01); *B01J 2208/00539* (2013.01)
(58) Field of Classification Search
    CPC .... B01J 2208/00008; B01J 2208/00017; B01J 2208/00026; B01J 2208/00539; C07C 29/00; C07C 29/128; C07C 29/1285; C07C 68/00; C07C 68/06; C07C 68/065
    See application file for complete search history.

(56) References Cited

U.S. PATENT DOCUMENTS

| | | |
|---|---|---|
| 2003/0045739 A1 | 3/2003 | Buchanan et al. |
| 2013/0035497 A1 | 2/2013 | Horng |

FOREIGN PATENT DOCUMENTS

| | | |
|---|---|---|
| CN | 102513158 A | 6/2012 |
| CN | 104761429 A | 7/2015 |

OTHER PUBLICATIONS

Kim et al., Synthesis of dimethyl carbonate from ethylene carbonate and methanol using immobilized ionic liquid on amorphous silica, 2010, Journal of Industrial and Engineering Chemistry, 16, 474-478. (Year: 2010).*
Translation of JP OA, pp. 1-7, Filed Jun. 24, 2021.
Translation of CN OA, pp. 1-10, Filed Jun. 24, 2021.
International Search Report and Written Opinion Form PCT/ISA/210 and PCT/ISA237, International Application No. PCT/CN2017/101784, pp. 1-9, International Filing Date Sep. 14, 2017, dated Mar. 19, 2018.
2010 (Aug. 28, 2010), 27(8), pp. 1059-1062, p. 1059,1060, left column, the first paragraph, and figure 1. (TIAN, multi-objective optimization of EG/DMC co-production Chemistry) Aug. 28 right column, the last paragraph to page Xiao et al. Design and process. Computers and Applied ZAK jiflifi'l-fk. 15 left column, the last paragraph but one, via Carbon Dioxide and The Chinese Journal of Process.
Apr. 2012 (Apr. 15, 2012), 12 (2), pp. 302-309, p. 302, lines 4-6. (Wu, Qinghai et al. Synthesis of Ethylene Carbonate Ethylene Oxide Catalyzed by Immobilized Ionic Liquid. Engineering).

* cited by examiner

SYSTEM AND PROCESS FOR CO-PRODUCING DIMETHYL CARBONATE AND ETHYLENE GLYCOL

The present application is a national stage application under 35 U.S.C. 371 based on international patent application PCT/CN2017/101784, now WO 2018/233093, filed on Sep. 14, 2017, which claims the priority of Chinese Patent Application No. 201710470046.3, filed on Jun. 20, 2017, disclosures of both of which are incorporated in the present application by reference in their entireties.

TECHNICAL FIELD

The present invention belongs to the technical field of chemical industry, and specifically relates to a system and a process for co-producing dimethyl carbonate and ethylene glycol.

BACKGROUND

Dimethyl Carbonate (DMC) is a nontoxic chemical raw material with excellent environmental performance and wide application, and is an important organic synthesizing intermediate. DMC contains functional groups such as carbonyl, methyl and methoxy in the molecular structure, and thus has multiple reaction properties.

Ethylene Glycol (EG) may be used as a solvent and an antifreeze. Moreover, polyethylene glycol, which is a high polymer of ethylene glycol, has good water solubility and good intermiscibility with a plurality of organic components. Polyethylene glycol has extremely wide applications in the industries such as cosmetics, pharmacy, chemical fiber, rubber, plastics, papermaking, paint, electroplating, pesticide, metal processing and food processing.

In general, industrially, ethylene oxide is used to react with carbon dioxide to produce ethylene carbonate, which is then subjected to alcoholysis reaction with methanol to produce dimethyl carbonate and ethylene glycol.

Ethylene oxide is very active in chemical nature and can undergo ring-opening addition reactions with many compounds. During the ring opening with carbon dioxide for generating ethylene carbonate, a lot of heat is also released, thus the reaction heat needs to be removed in time during the reaction, in order to avoid the catalyst from being deactivated at high temperature. In the conventional process for preparing dimethyl carbonate and ethylene glycol in which ethylene oxide is employed as a raw material, a homogeneous catalyst is usually used to catalyze the production of ethylene carbonate from ethylene oxide and carbon dioxide. The catalyst is necessarily separated and then recycled before entering alcoholysis reaction in order to reduce the production cost. Meanwhile, as ethylene carbonate has the characteristics such as high boiling point and low vapor pressure, higher vacuum degree and energy consumption are required when it is separated from the catalyst. CN 1432557A discloses a method for producing ethylene carbonate in an intermittent reaction kettle. The method has high reaction conversion rate of ethylene oxide, nevertheless it needs a subsequent procedure for separating and recycling ethylene carbonate and the catalyst, and thus has complex process and high energy consumption. U.S. Pat. No. 4,233,221 discloses a production process by a gas-phase fixed bed, wherein a mixed gas composed of ethylene oxide and a large amount of carbon dioxide is subjected to contact and reaction in a reactor. The yield of ethylene carbonate is only 87%, the heat released by the reaction is completely taken out by the generated ethylene carbonate, thus the bed temperature is not easy to control. In addition, the generated ethylene carbonate is subjected to subsequent operations after necessary removal of a large amount of residual ethylene oxide, thus the process flow is complicated.

The separated and purified ethylene carbonate enters an alcoholysis unit to react with methanol to generate dimethyl carbonate and ethylene glycol. Since this reaction is an equilibrium reaction, the conversion rate of ethylene carbonate is susceptible to chemical equilibrium. In order to increase the utilization ratio of the raw materials, it is common practice in industry that the unreacted methanol mixed in the products of dimethyl carbonate and/or ethylene glycol is purified and then fed back to the alcoholysis unit. However, the methanol fed back cannot be pure, and it inevitably contains the products of dimethyl carbonate and ethylene glycol. If the purity of the methanol fed back is too low, the shift in the chemical equilibrium of the reaction between dimethyl carbonate and ethylene glycol is affected, resulting in a decrease in the conversion rate of ethylene carbonate (yields of dimethyl carbonate and ethylene glycol). In order not to affect the conversion rate of ethylene carbonate, it is generally required that the methanol fed back has a higher purity. For example, in CN 1102826A it is required that the purity of the methanol fed back is not less than 99 wt %. However, this also means that higher energy is consumed for the purification of methanol.

Therefore, how to avoid the traditional procedure of separating the homogeneous catalyst from ethylene carbonate, simplify the process flow, and reduce the purity of the methanol fed back to reduce the energy consumption on the premise of not affecting the conversion rate of ethylene carbonate is a problem urgently to be solved in the field.

SUMMARY

In view of the deficiencies of the existing technologies, the present invention aims to provide a system and a process for co-producing dimethyl carbonate and ethylene glycol. The process improves the conversion rate of ethylene oxide, and also avoids the traditional procedure for separating a homogeneous catalyst from ethylene carbonate, so as to reduce the energy consumption of the process, and simplify the process flow.

To achieve this purpose, the present invention adopts the following technical solutions:

In a first aspect, the present invention provides a system for co-producing dimethyl carbonate and ethylene glycol, comprising an ethylene carbonate preparation unit and an ethylene carbonate alcoholysis unit which are connected with each other;

the ethylene carbonate preparation unit comprises a fixed bed reactor and a light-component removal tank which are connected with each other;

the fixed bed reactor is filled with an immobilized ionic liquid catalyst.

The immobilized ionic liquid catalyst is preferably any one or at least two selected from the immobilized ionic liquid catalysts disclosed in CN 102516220A, CN 101318949A, CN 103172608A, CN 102391241A or CN 102336736A.

As a preferred technical solution, the fixed bed reactor is provided with a heat removal device.

The reaction of carbon dioxide with ethylene oxide is an exothermic reaction and the fixed bed reactor needs heat removal to avoid catalyst deactivation. The heat removal means of the present invention is not particularly limited, and examples thereof which may be enumerated include: heat removal using circulating water, and use of heat for preheating of raw materials.

Preferably, a top feed outlet of the light-component removal tank is connected to a carbon dioxide feed inlet of the fixed bed reactor.

Preferably, a compressor is disposed on a pipeline between the top feed outlet of the light-component removal tank and the carbon dioxide feed inlet of the fixed bed reactor.

As a preferred technical solution, the ethylene carbonate alcoholysis unit comprises a reactive rectification column.

Preferably, a bottom feed outlet of the light-component removal tank is connected to an ethylene carbonate feed inlet of the reactive rectification column, and an alcoholysis reaction catalyst feed inlet is disposed on a pipeline between the bottom feed outlet of the light-component removal tank and the ethylene carbonate feed inlet of the reactive rectification column.

Preferably, the ethylene carbonate feed inlet of the reactive rectification column is higher than a methanol feed inlet.

Through adjusting the position of the ethylene carbonate feed inlet and the methanol feed inlet, ethylene carbonate and methanol are capable of countercurrent contact in the reactive rectification column, and the reaction is more complete, so that the conversion rate of ethylene carbonate is improved.

As a preferred technical solution, the system further comprises a dimethyl carbonate refining unit connected to the ethylene carbonate alcoholysis unit.

Preferably, the dimethyl carbonate refining unit comprises a high-pressure concentration column and a low-pressure refining column which are connected with each other.

Preferably, a top feed outlet of the reactive rectification column is connected to a feed inlet of the high-pressure concentration column, and a bottom feed outlet of the high-pressure concentration column is connected to a feed inlet of the low-pressure refining column.

Preferably, a top feed outlet of the high-pressure concentration column is connected to the methanol feed inlet of the reactive rectification column.

The material steam at the top of the high-pressure concentration column has higher temperature, and is capable of heat coupling integration with a reboiler of the reactive rectification column or a reboiler of the low-pressure refining column and the like so as to reduce the energy consumption of the process.

Preferably, a top feed outlet of the low-pressure refining column is connected to the feed inlet of the high-pressure concentration column.

As a preferred technical solution, the system further comprises an ethylene glycol refining unit connected with the ethylene carbonate alcoholysis unit.

Preferably, the ethylene glycol refining unit comprises an ethylene glycol light-component removal column, a hydrolysis reactor and an ethylene glycol refining column which are connected in sequence.

Preferably, a bottom feed outlet of the reactive rectification column is connected to a feed inlet of the ethylene glycol light-component removal column, a bottom feed outlet of the ethylene glycol light-component removal column is connected to a feed inlet of the hydrolysis reactor, and a feed outlet of the hydrolysis reactor is connected to a feed inlet of the ethylene glycol refining column.

Preferably, a top feed outlet of the ethylene glycol refining column is connected to the methanol feed inlet of the reactive rectification column.

In a further aspect, the present invention provides a process for co-producing dimethyl carbonate and ethylene glycol by using the system described above, comprising the following steps:

(1) Carbon dioxide and ethylene oxide as raw materials are introduced into the fixed bed reactor so that the two are contacted and reacted to generate ethylene carbonate, and the reaction product and unreacted raw materials are fed into the light-component removal tank for separation; and (2) The ethylene carbonate is extracted from the bottom of the light-component removal tank, and mixed with an alcoholysis reaction catalyst, followed by reacting with methanol in a reactive rectification column to generate dimethyl carbonate and ethylene glycol.

The present invention employs a fixed bed reactor filled with an immobilized ionic liquid catalyst for preparing ethylene carbonate, the reaction is more sufficient, which is capable of improving the conversion rate of the ethylene oxide. The immobilized ionic liquid catalyst would not be entrained out by the reaction product, so the traditional procedure for separating a homogeneous catalyst from ethylene carbonate was avoided, the energy consumption of the process was reduced, and the process flow was simplified.

As a preferred technical solution, the process further comprises: the carbon dioxide extracted from the top of the light-component removal tank is pressurized by a compressor and then fed back to the fixed bed reactor.

Preferably, the feeding molar ratio of carbon dioxide to ethylene oxide in step (1) is 1.2-10:1, and may be, e.g., 1.2:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1 or 10:1 and the like.

Preferably, the pressure within the fixed bed reactor is 1.5-6 MPa, and may be, e.g., 1.5 MPa, 2 MPa, 2.5 MPa, 3 MPa, 3.5 MPa, 4 MPa, 4.5 MPa, 5 MPa, 5.5 MPa or 6 MPa and the like; and the temperature is 80 to 200° C., and may be, e.g., 80° C., 90° C., 100° C., 110° C., 120° C., 130° C., 140° C., 150° C., 160° C., 170° C., 180° C., 190° C. or 200° C. and the like.

Preferably, the pressure within the light-component removal tank is 1-100 kPa, and may be, e.g., 1 kPa, 10 kPa, 20 kPa, 30 kPa, 40 kPa, 50 kPa, 60 kPa, 70 kPa, 80 kPa, 90 kPa or 100 kPa and the like; and the temperature is 50-200° C., and may be, e.g., 50° C., 60° C., 70° C., 80° C., 90° C., 100° C., 110° C., 120° C., 130° C., 140° C., 150° C., 160° C., 170° C., 180° C., 190° C. or 200° C. and the like.

As a preferred technical solution, the alcoholysis reaction catalyst in step (2) is one selected from the group consisting of an alkali metal oxide, an alkali metal hydroxide, an alkali metal carbonate, an alkoxide, an ionic liquid, and a combination of at least two selected therefrom.

Preferably, the feeding molar ratio of ethylene carbonate to the alcoholysis reaction catalyst is 100-1000:1, and may be, e.g., 100:1, 200:1, 300:1, 400:1, 500:1, 600:1, 700:1, 800:1, 900:1 or 1000:1 and the like.

Preferably, the feeding molar ratio of ethylene carbonate to methanol is 1:7-32, and may be, e.g., 1:7, 1:8, 1:9, 1:10, 1:12, 1:15, 1:18, 1:20, 1:22, 1:25, 1:28, 1:30 or 1:32 and the like.

Preferably, the pressure within the reactive rectification column is 100-400 kPa, and may be, e.g., 100 kPa, 120 kPa, 150 kPa, 180 kPa, 200 kPa, 220 kPa, 250 kPa, 280 kPa, 300 kPa, 320 kPa, 350 kPa, 380 kPa or 400 kPa and the like; the temperature at the column top is 60-110° C., and may be, e.g., 60° C., 65° C., 70° C., 75° C., 80° C., 85° C., 90° C., 95° C. or 100° C. and the like; and the temperature at the column bottom is 80-130° C., and may be, e.g., 80° C., 85°

C., 90° C., 95° C., 100° C., 105° C., 110° C., 115° C., 120° C., 125° C. or 130° C. and the like.

In order to increase the utilization ratio of the raw materials, it is common practice in industry that the unreacted methanol mixed in the products of dimethyl carbonate and/or ethylene glycol is purified and then fed back to the reactive rectification column. However, the methanol fed back cannot be pure, and it inevitably contains the products of dimethyl carbonate and ethylene glycol. If the purity of the methanol fed back is too low, the shift in the chemical equilibrium of the reaction between dimethyl carbonate and ethylene glycol is affected, resulting in a decrease in the conversion rate of ethylene carbonate (yields of dimethyl carbonate and ethylene glycol). In order not to affect the conversion rate of ethylene carbonate, it is generally required that the purity of the methanol fed back is not less than 99 wt %. Nevertheless, this also means that higher energy consumption is required for the purification of methanol. By adjusting the pressure, the temperature and the reflux ratio within the reactive rectification column, the present invention can reduce the requirement on the purity of the returned methanol to 90 wt % and reduce the energy consumption on the premise of ensuring the conversion rate of the ethylene carbonate.

As a preferred technical solution, the process further comprises a dimethyl carbonate purification step.

Preferably, the dimethyl carbonate purification step comprises: an azeotrope of dimethyl carbonate and methanol is extracted from the top of the reactive rectification column, and fed into a high-pressure concentration column and a low-pressure refining column in sequence for separation; the methanol extracted from the top of the high-pressure concentration column is fed back to the reactive rectification column, and the mixture of dimethyl carbonate and methanol extracted from the top of the low-pressure refining column is fed back to the high-pressure concentration column, and dimethyl carbonate is extracted from the bottom of the low-pressure refining column.

Preferably, the pressure within the high-pressure concentration column is 0.5-6 MPa, and may be, e.g., 0.5 MPa, 1 MPa, 1.5 MPa, 2 MPa, 2.5 MPa, 3 MPa, 3.5 MPa, 4 MPa, 4.5 MPa, 5 MPa, 5.5 MPa or 6 MPa and the like; and the temperature at the column top is 10-150° C. higher than the temperature at the column bottom of the reactive rectification column, and it may be, e.g., 10° C., 20° C., 30° C., 40° C., 50° C., 60° C., 70° C., 80° C., 90° C., 100° C., 110° C., 120° C., 130° C. or 140° C. and the like.

Preferably, the concentration of the methanol extracted from the top of the high-pressure concentration column is 90-99.9 wt %, and may be, e.g., 90 wt %, 91 wt %, 92 wt %, 93 wt %, 94 wt %, 95 wt %, 96 wt %, 97 wt %, 98 wt %, 98.5 wt %, 99 wt %, 99.5 wt % or 99.9 wt % and the like.

Preferably, the pressure within the low-pressure refining column is 0.1-1 MPa, and may be, e.g., 0.1 MPa, 0.2 MPa, 0.3 MPa, 0.4 MPa, 0.5 MPa, 0.6 MPa, 0.7 MPa, 0.8 MPa, 0.9 MPa or 1 MPa and the like.

As a preferred technical solution, the process further comprises an ethylene glycol purification step.

Preferably, the ethylene glycol purification step comprises: a mixture of ethylene glycol, methanol, ethylene carbonate and the alcoholysis reaction catalyst is extracted from the bottom of the reactive rectification column, and fed into an ethylene glycol light-component removal column, a hydrolysis reactor and an ethylene glycol refining column in sequence for separation, hydrolysis and refinement, and the methanol extracted from the top of the ethylene glycol light-component removal column is fed back to the reactive rectification column, and ethylene glycol is extracted from the side line of the ethylene glycol refining column.

In the present invention, a small amount of unreacted ethylene carbonate is subjected to hydrolysis reaction in the hydrolysis reactor to generate ethylene glycol and carbon dioxide, and the carbon dioxide is discharged from a gas bag of the hydrolysis reactor.

Preferably, the pressure within the ethylene glycol light-component removal column is 1-80 kPa, and may be, e.g., 1 kPa, 10 kPa, 20 kPa, 30 kPa, 40 kPa, 50 kPa, 60 kPa, 70 kPa or 80 kPa and the like; and the operating temperature is 20-180° C., and may be, e.g., 20° C., 30° C., 40° C., 50° C., 60° C., 70° C., 80° C., 90° C., 100° C., 110° C., 120° C., 130° C., 140° C., 150° C., 160° C., 170° C. or 180° C. and the like.

Preferably, the pressure within the hydrolysis reactor is 110-900 kPa, and may be, e.g., 110 kPa, 150 kPa, 200 kPa, 300 kPa, 400 kPa, 500 kPa, 600 kPa, 700 kPa, 800 kPa or 900 kPa and the like; and the operating temperature is 50-180° C., and may be, e.g., 50° C., 60° C., 70° C., 80° C., 90° C., 100° C., 110° C., 120° C., 130° C., 140° C., 150° C., 160° C., 170° C. or 180° C. and the like.

Preferably, the pressure within the ethylene glycol refining column is 1-80 kPa, and may be, e.g., 1 kPa, 10 kPa, 20 kPa, 30 kPa, 40 kPa, 50 kPa, 60 kPa, 70 kPa or 80 kPa and the like; and the operating temperature is 35-190° C., and may be, e.g., 35° C., 40° C., 50° C., 60° C., 70° C., 80° C., 90° C., 100° C., 110° C., 120° C., 130° C., 140° C., 150° C., 160° C., 170° C., 180° C. or 190° C. and the like.

As compared to the existing technologies, the present invention has the following beneficial effects:

The present invention employs a fixed bed reactor filled with an immobilized ionic liquid catalyst for preparing ethylene carbonate, the reaction is more sufficient, so that the conversion rate of the ethylene oxide reaches 99-99.9%. The immobilized ionic liquid catalyst would not be entrained out by the reaction product, so the traditional procedure for separating a homogeneous catalyst from ethylene carbonate is avoided, the energy consumption of the process is reduced, and the process flow is simplified.

By adjusting the process conditions within the reactive rectification column, the requirement on the purity of the returned methanol can be reduced to 90 wt % while the conversion rate of the ethylene carbonate is ensured to be more than or equal to 99%, so that the energy consumption is reduced.

Figure 1:
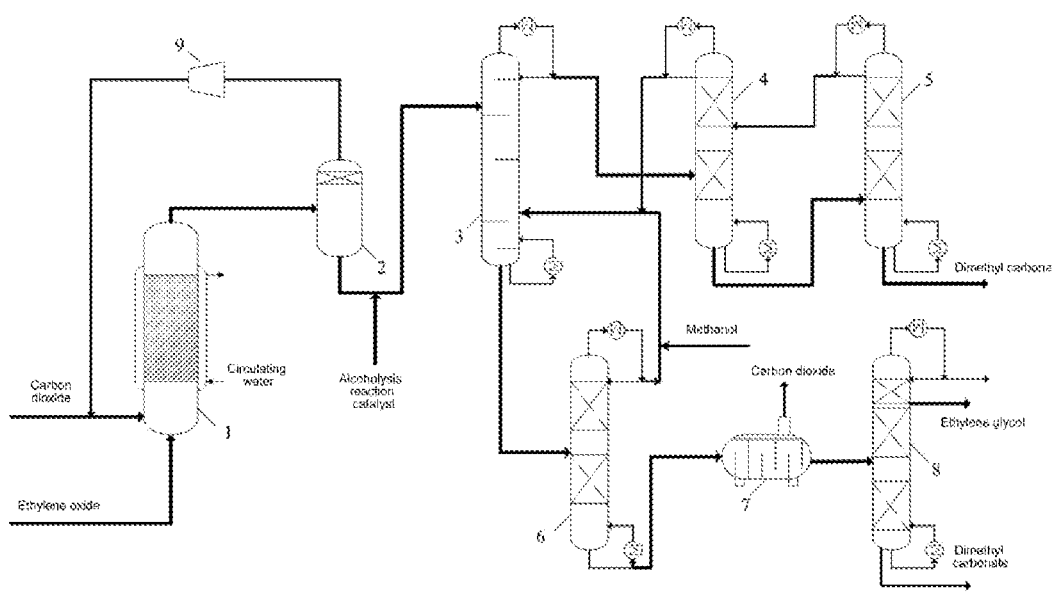
FIG. 1 is a structural view of a system for co-producing dimethyl carbonate and ethylene glycol provided by Example 1 of the present invention.

including: 1—fixed bed reactor, 2—light-component removal tank, 3—reactive rectification column, 4—high-pressure concentration column, 5—low-pressure refining column, 6—ethylene glycol light-component removal column, 7—hydrolysis reactor, 8—ethylene glycol refining column, 9—compressor, and the arrows shown in the FIGURE indicate the flow directions of the materials.

DETAILED DESCRIPTION

The technical solution of the present invention is further illustrated by the specific embodiments below. Those skilled in the art shall understand that the specific embodiments are set forth to aid in understanding the present invention and should not be regarded as specific limitations to the present invention.

The purities of the raw materials used in the following examples are respectively: 99.999% of carbon dioxide, 99.995% of ethylene oxide and 99.9% of methanol. The immobilized ionic liquid catalyst is hydroxyl imidazole ionic liquid catalyst loaded by polystyrene resin; and the catalyst for the alcoholysis reaction of ethylene carbonate is sodium methoxide.

Example 1

A system for co-producing dimethyl carbonate and ethylene glycol, as shown in FIG. 1, comprises a fixed bed reactor 1, a light-component removal tank 2, a reactive rectification column 3, a high-pressure concentration column 4, a low-pressure refining column 5, an ethylene glycol light-component removal column 6, a hydrolysis reactor 7, an ethylene glycol refining column 8 and a compressor 9.

Wherein, an outlet of the fixed bed reactor 1 is connected to a feed inlet of the light-component removal tank 2.

A top feed outlet of the light-component removal tank 2 is connected to a carbon dioxide feed inlet of the fixed bed reactor 1, and the compressor 9 is disposed on the pipeline.

A bottom feed outlet of the light-component removal tank 2 is connected to an ethylene carbonate feed inlet of the reactive rectification column 3, and an alcoholysis reaction catalyst feed inlet is disposed on a pipeline between the bottom feed outlet of the light-component removal tank 2 and the ethylene carbonate feed inlet of the reactive rectification column 3.

The ethylene carbonate feed inlet of the reactive rectification column 3 is higher than a methanol feed inlet.

A top feed outlet of the reactive rectification column 3 is connected to a feed inlet of the high-pressure concentration column 4, a bottom feed outlet of the high-pressure concentration column 4 is connected to a feed inlet of the low-pressure refining column 5, a top feed outlet of the high-pressure concentration column 4 is connected to the methanol feed inlet of the reactive rectification column 3, and a top feed outlet of the low-pressure refining column 5 is connected to the feed inlet of the high-pressure concentration column 4.

A bottom feed outlet of the reactive rectification column 3 is connected to a feed inlet of the ethylene glycol light-component removal column 6, a top feed outlet of the ethylene glycol light-component removal column 6 is connected to the methanol feed inlet of the reactive rectification column 3, a bottom feed outlet of the ethylene glycol light-component removal column 6 is connected to a feed inlet of the hydrolysis reactor 7, and a feed outlet of the hydrolysis reactor 7 is connected to a feed inlet of the ethylene glycol refining column 8.

Example 2

A process for co-producing dimethyl carbonate and ethylene glycol by using the system provided by Example 1, comprising the following steps:

(1) Carbon dioxide and ethylene oxide as raw materials were continuously introduced into the fixed bed reactor 1 so that the two were contacted and reacted to generate ethylene carbonate, and the reaction product and unreacted raw materials were fed into the light-component removal tank 2 for separation; the carbon dioxide extracted from the top of the light-component removal tank 2 was pressurized by the compressor 9, and then recycled into the fixed bed reactor 1 to be involved in a further reaction;

wherein the feeding rate of carbon dioxide was 13 kg/h, and the feeding rate of ethylene oxide was 6 kg/h; the pressure within the fixed bed reactor 1 was 3 MPa and the temperature was 125° C.; the pressure within the light-component removal tank 2 was 40 kPa and the temperature was 100° C.;

the composition of the mixture extracted from the outlet of the fixed-bed reactor 1 was 66.27 wt % of ethylene carbonate, 33.53 wt % of carbon dioxide and 0.2 wt % of ethylene oxide, and the conversion rate of ethylene oxide was 99.7%;

(2) The ethylene carbonate was extracted from the bottom of the light-component removal tank 2, and mixed with sodium methoxide introduced from an alcoholysis reaction catalyst feed inlet; and the mixture was fed into the reactive rectification column 3 from the ethylene carbonate feed inlet at the upper part, and came in countercurrent contact with methanol introduced from the methanol feed inlet at the lower part to perform alcoholysis reaction to generate dimethyl carbonate and ethylene glycol;

wherein the feeding rate of ethylene carbonate was 11.9 kg/h, the feeding rate of sodium methoxide was 0.012 kg/h, and the feeding rate of methanol was 50.9 kg/h; the pressure within the reactive rectification column 3 was 100 kPa, the temperature at the column top was 63.4° C., the temperature at the column bottom was 90° C., the reflux ratio was 0.5, and the heat load of the column kettle was 0.15 kW;

the content of ethylene carbonate in the reactive rectification column 3 was 0.028 wt %, and the conversion rate of ethylene carbonate was 99.8%;

(3) 46.7 kg/h of an azeotrope of dimethyl carbonate and methanol was extracted from the top of the reactive rectification column 3, and fed into the high-pressure concentration column 4 for concentration, and the methanol extracted from the top of the high-pressure concentration column 4 was fed back to the reactive rectification column 3 to be involved in a further reaction; the concentrated dimethyl carbonate solution extracted from the bottom of the high-pressure concentration column 4 was fed into the low-pressure refining column 5 for refining, the mixture of dimethyl carbonate and methanol extracted from the top of the low-pressure refining column 5 was fed back to the high-pressure concentration column 4, and 12.1 kg/h of dimethyl carbonate was extracted from the bottom of the low-pressure refining column 5;

wherein the pressure within the high-pressure concentration column 4 was 1600 kPa, the temperature at the column top was 150.3° C., and the purity of the methanol extracted from the top was 90 wt %; the pressure within the low-pressure refining column 5 was 400 kPa, the temperature at the column top was 110° C., and the temperature at the column bottom was 140° C.;

(4) 12.2 kg/h of a mixture of ethylene glycol, methanol, ethylene carbonate and an alcoholysis catalyst was extracted from the bottom of the reactive rectification column 3, and fed into the ethylene glycol light-component removal column 6 for separation; 3.8 kg/h of methanol extracted from the top of the ethylene glycol light-component removal column 6 was fed back to the reactive rectification column 3 to be involved in a further reaction; 8.4 kg/h of an ethylene glycol mixed solution (containing 0.7 wt % of ethylene carbonate) extracted from the bottom of the ethylene glycol light-component removal column 6 was fed into the hydrolysis reactor 7 for hydrolysis, and finally fed into the ethylene glycol refining column 8 for refining; heavy components (diethylene glycol, triethylene glycol and sodium methoxide) were extracted from the bottom of the ethylene glycol refining column 8, and ethylene glycol with a purity of more than 99.9% was extracted from the side line of the ethylene glycol refining column 8;

wherein the pressure within the ethylene glycol light-component removal column 6 was 23 kPa, the temperature at the column top was 49.4° C., and the temperature at the column bottom was 151° C.; the pressure within the hydrolysis reactor 7 was 800 kPa and the operating temperature was 160° C.; the pressure within the ethylene glycol refining column 8 was 10 kPa and the temperature at the column top was 120.6° C.

This example employed a fixed bed reactor filled with an immobilized ionic liquid catalyst for preparing ethylene carbonate, so that the conversion rate of the ethylene oxide reached 99.7%. Moreover, the traditional procedure for separating a homogeneous catalyst from ethylene carbonate was avoided, the energy consumption of the process was reduced, and the process flow was simplified.

By adjusting the process conditions within the reactive rectification column, the conversion rate of the ethylene carbonate was still 99.8% when the purity of the returned methanol was 90 wt %, which reduced the energy consumption during purifying the methanol.

Example 3

The present process conditions were the same as those in Example 2, except that the pressure within the fixed bed reactor 1 was 2.5 MPa and the temperature was 110° C.; the pressure in the reactive rectification column 3 was 200 kPa, the temperature at the column top was 82° C., and the temperature at the column bottom was 107° C.

This example employed a fixed bed reactor filled with an immobilized ionic liquid catalyst for preparing ethylene carbonate, so that the conversion rate of the ethylene oxide reached 99.3%. Moreover, the traditional procedure for separating a homogeneous catalyst from the ethylene carbonate was avoided, the energy consumption of the process was reduced, and the process flow was simplified.

By adjusting the process conditions within the reactive rectification column, the conversion rate of the ethylene carbonate was still 99.4% when the purity of the returned methanol was 90.4 wt %, which reduced the energy consumption during purifying the methanol.

Example 4

The present process conditions were the same as those in Example 2, except that the pressure within the fixed bed reactor 1 was 2.7 MPa and the temperature was 120° C.; the pressure within the reactive rectification column 3 was 300 kPa, the temperature at the column top was 93° C., and the temperature at the column bottom was 118° C.

This example employed a fixed bed reactor filled with an immobilized ionic liquid catalyst for preparing ethylene carbonate, so that the conversion rate of the ethylene oxide reached 99.5%. Moreover, the traditional procedure for separating a homogeneous catalyst from the ethylene carbonate was avoided, the energy consumption of the process was reduced, and the process flow was simplified.

By adjusting the process conditions within the reactive rectification column, the conversion rate of the ethylene carbonate was still 99% when the purity of the returned methanol was 90.5 wt %, which reduced the energy consumption during purifying the methanol.

Example 5

The present process conditions were the same as those in Example 2, except that the pressure within the fixed bed reactor 1 was 1.5 MPa and the temperature was 80° C.; the pressure within the reactive rectification column 3 was 400 kPa, the temperature at the column top was 110° C., and the temperature at the column bottom was 130° C.

This example employed a fixed bed reactor filled with an immobilized ionic liquid catalyst for preparing ethylene carbonate, so that the conversion rate of the ethylene oxide reached 99.0%. Moreover, the traditional procedure for separating a homogeneous catalyst from ethylene carbonate was avoided, the energy consumption of the process was reduced, and the process flow was simplified.

By adjusting the process conditions within the reactive rectification column, the conversion rate of the ethylene carbonate was still 99.3% when the purity of the returned methanol was 90.6 wt %, which reduced the energy consumption during purifying the methanol.

Example 6

The present process conditions were the same as those in Example 2, except that the pressure within the fixed bed reactor 1 was 6 MPa and the temperature was 200° C.; the pressure within the reactive rectification column 3 was 110 kPa, the temperature at the column top was 60° C., and the temperature at the column bottom was 80° C.

This example employed a fixed bed reactor filled with an immobilized ionic liquid catalyst for preparing ethylene carbonate, so that the conversion rate of the ethylene oxide reached 99.6%. Moreover, the traditional procedure for separating a homogeneous catalyst from the ethylene carbonate was avoided, the energy consumption of the process was reduced, and the process flow was simplified.

By adjusting the process conditions within the reactive rectification column, the conversion rate of the ethylene carbonate was still 99.5% when the purity of the returned methanol was 90.1 wt %, which reduced the energy consumption during purifying the methanol.

Comparison Example 1

The present process conditions were the same as those in Example 2, except that the pressure within the reactive rectification column 3 was 500 kPa, the temperature at the column top was 115° C., and the temperature at the column bottom was 140° C.

Since the process conditions in the reactive rectification column 3 in Comparison Example 1 were not within the ranges defined by the present invention and the purity of the returned methanol was lower (90 wt %), the conversion rate of ethylene carbonate was reduced to 97%.

Comparison Example 2

The present process conditions were the same as those in Example 2, except that the pressure within the reactive rectification column 3 was 80 kPa, the temperature at the column top was 55° C., and the temperature at the column bottom was 75° C.

Since the process conditions in the reactive rectification column 3 in Comparison Example 2 were not within the ranges defined by the present invention and the purity of the returned methanol was lower (90 wt %), the conversion rate of ethylene carbonate was reduced to 95%.

The applicant has stated that the above examples are only specific embodiments of the present invention, but the protection scope of the present invention is not limited thereto. It should be apparent to those skilled in the art that any varieties or alternatives that can be easily conceived by those skilled in the art within the disclosure scope of the present invention falls within the protection scope and the disclosure scope of the present invention.

What is claimed is:

1. A system for co-producing dimethyl carbonate and ethylene glycol, comprising an ethylene carbonate preparation unit and an ethylene carbonate alcoholysis unit which are connected with each other;
    the ethylene carbonate preparation unit comprises a fixed bed reactor and a light-component removal tank which are connected with each other; and
    the fixed bed reactor is filled with an immobilized ionic liquid catalyst.

2. The system according to claim 1, wherein the fixed bed reactor is provided with a heat removal device.

3. The system according to claim 1, wherein a top feed outlet of the light-component removal tank is connected to a carbon dioxide feed inlet of the fixed bed reactor.

4. The system according to claim 1, wherein a compressor is disposed on a pipeline between the top feed outlet of the light-component removal tank and the carbon dioxide feed inlet of the fixed bed reactor.

5. The system according to claim 1, wherein the ethylene carbonate alcoholysis unit comprises a reactive rectification column.

6. The system according to claim 5, wherein a bottom feed outlet of the light-component removal tank is connected to an ethylene carbonate feed inlet of the reactive rectification column, and an alcoholysis reaction catalyst feed inlet is disposed on a pipeline between the bottom feed outlet of the light-component removal tank and the ethylene carbonate feed inlet of the reactive rectification column;
    the ethylene carbonate feed inlet of the reactive rectification column is higher than a methanol feed inlet.

7. The system according to claim 6, further comprising a dimethyl carbonate refining unit connected with the ethylene carbonate alcoholysis unit.

8. The system according to claim 7, wherein the dimethyl carbonate refining unit comprises a high-pressure concentration column and a low-pressure refining column which are connected with each other.

9. The system according to claim 8, wherein a top feed outlet of the reactive rectification column is connected with a feed inlet of the high-pressure concentration column, and a bottom feed outlet of the high-pressure concentration column is connected to the feed inlet of the low-pressure refining column;
    a top feed outlet of the high-pressure concentration column is connected to the methanol feed inlet of the reactive rectification column;
    a top feed outlet of the low-pressure refining column is connected to the feed inlet of the high-pressure concentration column.

10. The system according to claim 6, further comprising an ethylene glycol refining unit connected with the ethylene carbonate alcoholysis unit.

11. The system according to claim 10, wherein the ethylene glycol refining unit comprises an ethylene glycol light-component removal column, a hydrolysis reactor and an ethylene glycol refining column which are connected in sequence.

12. The system according to claim 11, wherein a bottom feed outlet of the reactive rectification column is connected to a feed inlet of the ethylene glycol light-component removal column, a bottom feed outlet of the ethylene glycol light-component removal column is connected to a feed inlet of the hydrolysis reactor, and a feed outlet of the hydrolysis reactor is connected to a feed inlet of the ethylene glycol refining column;
    a top feed outlet of the ethylene glycol refining column is connected to the methanol feed inlet of the reactive rectification column.

13. A process for co-producing dimethyl carbonate and ethylene glycol by using the system according to claim 1, comprising the following steps:
    (1) carbon dioxide and ethylene oxide as raw materials are introduced into the fixed bed reactor so that the two are contacted and reacted to generate ethylene carbonate, and the reaction product and unreacted raw materials are fed into the light-component removal tank for separation; and
    (2) the ethylene carbonate is extracted from the bottom of the light-component removal tank, and mixed with an alcoholysis reaction catalyst, followed by reacting with methanol in a reactive rectification column to generate dimethyl carbonate and ethylene glycol.

14. The process according to claim 13, further comprising: the carbon dioxide extracted from the top of the light-component removal tank is pressurized by a compressor and then fed back to the fixed bed reactor.

15. The process according to claim 14, wherein the feeding molar ratio of carbon dioxide to ethylene oxide in step (1) is 1.2-10:1; the pressure within the fixed bed reactor is 1.5-6 MPa and the temperature is 80-200° C.; the pressure within the light-component removal tank is 1-100 kPa and the temperature is 50-200° C.

16. The process according to claim 13, wherein the alcoholysis reaction catalyst in step (2) is one selected from the group consisting of an alkali metal oxide, an alkali metal hydroxide, an alkali metal carbonate, an alkoxide, an ionic liquid, and a combination of at least two selected therefrom.

17. The process according to claim 14, wherein the feeding molar ratio of ethylene carbonate to the alcoholysis reaction catalyst is 100-1000:1;
    the feeding molar ratio of ethylene carbonate to methanol is 1:7-32;
    the pressure within the reactive rectification column is 100-400 kPa, the temperature at the column top is 60-110° C., and the temperature at the column bottom is 80-130° C.

18. The process according to claim 13, further comprising a dimethyl carbonate purification step.

19. The process according to claim 18, wherein the dimethyl carbonate purification step comprises: an azeotrope of dimethyl carbonate and methanol is extracted from the top of the reactive rectification column, and fed into a high-pressure concentration column and a low-pressure refining column in sequence for separation; the methanol extracted from the top of the high-pressure concentration column is fed back to the reactive rectification column, and the mixture of dimethyl carbonate and methanol extracted from the top of the low-pressure refining column is fed back to the high-pressure concentration column, and dimethyl carbonate is extracted from the bottom of the low-pressure refining column.

20. The process according to claim 19, wherein the pressure within the high-pressure concentration column is 0.5-6 MPa, and the temperature at the column top is 10-150° C. higher than the temperature at the column bottom of the reactive rectification column;

the concentration of the methanol extracted from the top of the high-pressure concentration column is 90-99.9 wt %;

the pressure within the low-pressure refining column is 0.1-1 MPa.

21. The process according to claim 13, further comprising an ethylene glycol purification step.

22. The process according to claim 21, wherein the ethylene glycol purification step comprises: a mixture of ethylene glycol, methanol, ethylene carbonate and the alcoholysis reaction catalyst is extracted from the bottom of the reactive rectification column, and fed into an ethylene glycol light-component removal column, a hydrolysis reactor and an ethylene glycol refining column in sequence for separation, hydrolysis and refinement, and the methanol extracted from the top of the ethylene glycol light-component removal column is fed back to the reactive rectification column, and ethylene glycol is extracted from the side line of the ethylene glycol refining column.

23. The process according to claim 22, wherein the pressure within the ethylene glycol light-component removal column is 1-80 kPa and the operating temperature is 20-180° C.;

the pressure within the hydrolysis reactor is 110-900 kPa and the operating temperature is 50-180° C.;

the pressure within the ethylene glycol refining column is 1-80 kPa and the operating temperature is 35-190° C.

\* \* \* \* \*